US009770311B2

(12) United States Patent
Zipprich et al.

(10) Patent No.: US 9,770,311 B2
(45) Date of Patent: Sep. 26, 2017

(54) DENTAL IMPLANT SYSTEM AND METHOD FOR PRODUCING A DENTAL IMPLANT SYSTEM

(76) Inventors: Holger Zipprich, Malchen (DE); Urs Brodbeck, Erlenbach (CH); Markus Schlee, Forchheim (DE)

( * ) Notice: Subject to any disclaimer, the term of this patent is extended or adjusted under 35 U.S.C. 154(b) by 189 days.

(21) Appl. No.: 13/885,643

(22) PCT Filed: Nov. 15, 2011

(86) PCT No.: PCT/EP2011/005748
§ 371 (c)(1),
(2), (4) Date: Jul. 19, 2013

(87) PCT Pub. No.: WO2012/065718
PCT Pub. Date: May 24, 2012

(65) Prior Publication Data
US 2015/0037759 A1    Feb. 5, 2015

(30) Foreign Application Priority Data
Nov. 15, 2010    (DE) ........................ 10 2010 051 176

(51) Int. Cl.
*A61C 8/00*    (2006.01)
*A61C 13/00*    (2006.01)

(52) U.S. Cl.
CPC ............ *A61C 8/0013* (2013.01); *A61C 8/005* (2013.01); *A61C 8/006* (2013.01); *A61C 8/0012* (2013.01);
(Continued)

(58) Field of Classification Search
CPC ....... A61C 13/00; A61C 8/005; A61C 8/0069; A61C 8/0012; A61C 8/0013; A61C 8/0059; A61C 8/0086
(Continued)

(56) References Cited

U.S. PATENT DOCUMENTS 4,270,905 A    6/1981    Mohammed
4,324,550 A    4/1982    Reuther et al.
(Continued)

FOREIGN PATENT DOCUMENTS

CH    642838        5/1984
CH    696 625 A5    8/2007
(Continued)

OTHER PUBLICATIONS

Official Action for U.S. Appl. No. 13/696,162 mailed Jul. 18, 2014, 20 pages.
(Continued)

*Primary Examiner* — Cris L Rodriguez
*Assistant Examiner* — Matthew Saunders
(74) *Attorney, Agent, or Firm* — Sheridan Ross PC

(57) ABSTRACT

A dental implant system having a first implant part, provided for introduction into a jawbone, and having a second implant part, provided for attaching a tooth replacement part, the implant parts being mechanically interconnectable via a connection pin which is integrally formed on one of the implant parts and which is insertable into a receiving duct provided in the other implant part, is to have a particularly high stability and long duration of use, even when ceramic materials are used for the implant parts. For this purpose, in a contact region to the receiving duct the connection pin is provided with a spacer formed of a material softer than the material of the connection pin, and the connection pin has a porous surface, in the surface region which is provided with the coating, to form a material fit connection to the coating.

31 Claims, 6 Drawing Sheets

(52) U.S. Cl.
CPC .......... *A61C 8/0068* (2013.01); *A61C 8/0069* (2013.01); *A61C 13/0007* (2013.01); *A61C 13/0018* (2013.01); *A61C 8/0022* (2013.01); *A61C 8/0086* (2013.01); *Y10T 29/49567* (2015.01)

(58) Field of Classification Search
USPC ............................................. 433/169–201.1
See application file for complete search history.

(56) References Cited

U.S. PATENT DOCUMENTS

| | | | |
|---|---|---|---|
| 4,731,085 A * | 3/1988 | Koch | 433/173 |
| 4,793,808 A | 12/1988 | Kirsch | |
| 4,832,601 A | 5/1989 | Linden | |
| 4,850,870 A | 7/1989 | Lazzara et al. | |
| 4,854,872 A | 8/1989 | Detsch | |
| 4,876,148 A * | 10/1989 | Virkar | 428/384 |
| 5,015,186 A | 5/1991 | Detsch | |
| 5,125,971 A * | 6/1992 | Nonami et al. | 106/35 |
| 5,135,395 A | 8/1992 | Marlin | |
| 5,195,892 A | 3/1993 | Gersberg | |
| 5,246,370 A | 9/1993 | Coatman | |
| 5,281,140 A | 1/1994 | Niznick | |
| 5,302,126 A | 4/1994 | Wimmer et al. | |
| 5,336,465 A * | 8/1994 | Matsunaga et al. | 419/2 |
| 5,407,359 A | 4/1995 | Balfour et al. | |
| 5,425,639 A * | 6/1995 | Anders | 433/169 |
| 5,437,551 A * | 8/1995 | Chalifoux | A61C 8/0018 |
| | | | 433/172 |
| 5,553,983 A | 9/1996 | Shinjo | |
| 5,674,072 A * | 10/1997 | Moser et al. | 433/173 |
| 5,766,179 A | 6/1998 | Faccioli et al. | |
| 5,782,918 A | 7/1998 | Klardie et al. | |
| 5,785,525 A | 7/1998 | Weissman | |
| 5,947,733 A | 9/1999 | Sutter et al. | |
| 5,954,505 A * | 9/1999 | Ford | A61C 8/0086 |
| | | | 433/173 |
| 5,984,680 A | 11/1999 | Rogers | |
| 5,989,026 A | 11/1999 | Rogers et al. | |
| 6,158,310 A | 12/2000 | Goss et al. | |
| 6,217,331 B1 | 4/2001 | Rogers et al. | |
| 6,419,489 B1 | 7/2002 | Jorneus et al. | |
| 6,500,003 B2 | 12/2002 | Nichinonni | |
| 6,537,069 B1 | 3/2003 | Simmons, Jr. | |
| 6,575,057 B1 | 6/2003 | Ploeger | |
| 6,652,765 B1 | 11/2003 | Beaty | |
| 7,144,622 B1 * | 12/2006 | Stecher et al. | 428/217 |
| 7,225,710 B2 | 6/2007 | Pacheco, Jr. | |
| 7,249,949 B2 | 7/2007 | Carter | |
| 7,309,231 B2 | 12/2007 | Engman | |
| 8,123,524 B2 | 2/2012 | Anitua Aldecoa | |
| 8,291,795 B2 | 10/2012 | Hughes et al. | |
| 8,347,761 B2 | 1/2013 | Goss et al. | |
| 8,932,663 B2 * | 1/2015 | Ritz et al. | 427/2.26 |
| 2002/0177105 A1 | 11/2002 | Engman | |
| 2003/0013068 A1 | 1/2003 | Gittleman | |
| 2003/0194679 A1 | 10/2003 | Odrich et al. | |
| 2003/0232309 A1 * | 12/2003 | Dinkelacker | A61C 8/005 |
| | | | 433/173 |
| 2004/0121285 A1 * | 6/2004 | Wu | 433/173 |
| 2004/0185417 A1 | 9/2004 | Rassoli | |
| 2004/0185419 A1 | 9/2004 | Schulter et al. | |
| 2005/0042573 A1 | 2/2005 | Lustig et al. | |
| 2005/0166724 A1 | 8/2005 | Castaneda | |
| 2005/0186537 A1 | 8/2005 | Gersberg | |
| 2006/0110706 A1 | 5/2006 | Jorneus et al. | |
| 2006/0141418 A1 | 6/2006 | Heo | |
| 2006/0172257 A1 | 8/2006 | Niznick | |
| 2007/0037121 A1 | 2/2007 | Carter | |
| 2008/0182227 A1 * | 7/2008 | Wolf et al. | 433/174 |
| 2008/0241789 A1 * | 10/2008 | Mundorf | 433/173 |
| 2008/0241792 A1 | 10/2008 | Rossler et al. | |
| 2008/0261176 A1 | 10/2008 | Hurson | |
| 2008/0261178 A1 * | 10/2008 | Homann et al. | 433/201.1 |
| 2008/0293015 A1 * | 11/2008 | Wong et al. | 433/180 |
| 2009/0035722 A1 * | 2/2009 | Balasundaram | A61F 2/30767 |
| | | | 433/201.1 |
| 2009/0075236 A1 | 3/2009 | Towse et al. | |
| 2009/0123889 A1 * | 5/2009 | Mehrhof | 433/173 |
| 2009/0123890 A1 | 5/2009 | Purga et al. | |
| 2009/0123891 A1 * | 5/2009 | Rosenberg | 433/174 |
| 2009/0239195 A1 | 9/2009 | Wohrle et al. | |
| 2009/0305190 A1 * | 12/2009 | Zipprich | 433/173 |
| 2010/0099058 A1 * | 4/2010 | Wang | 433/173 |
| 2010/0178636 A1 * | 7/2010 | Stephan et al. | 433/201.1 |
| 2010/0196851 A1 * | 8/2010 | Konig | 433/173 |
| 2010/0196852 A1 | 8/2010 | Baruc et al. | |
| 2010/0240009 A1 | 9/2010 | Gogarnoiu | |
| 2010/0304334 A1 * | 12/2010 | Layton | 433/173 |
| 2011/0065064 A1 * | 3/2011 | Kahdemann et al. | 433/174 |
| 2011/0123951 A1 * | 5/2011 | Lomicka | 433/174 |
| 2011/0212417 A1 * | 9/2011 | Beekmans | A61C 8/0022 |
| | | | 433/174 |
| 2011/0223562 A1 * | 9/2011 | Zipprich | 433/174 |
| 2011/0311947 A1 * | 12/2011 | Schoene | A61C 8/005 |
| | | | 433/174 |
| 2012/0288824 A1 * | 11/2012 | Nordin et al. | 433/173 |
| 2013/0108984 A1 | 5/2013 | Zipprich | |
| 2013/0337410 A1 | 12/2013 | Ten Bruggenkate | |
| 2014/0106305 A1 | 4/2014 | Jacoby et al. | |
| 2014/0134570 A1 | 5/2014 | Zipprich et al. | |
| 2014/0212844 A1 | 7/2014 | Zipprich | |
| 2015/0157427 A1 | 6/2015 | Purga et al. | |

FOREIGN PATENT DOCUMENTS

| | | |
|---|---|---|
| CN | 2216818 | 1/1996 |
| CN | 1889896 | 1/2007 |
| CN | 101146491 | 3/2008 |
| CN | 101188982 | 5/2008 |
| CN | 101252891 | 8/2008 |
| CN | 101878003 | 11/2010 |
| CN | 102202598 | 9/2011 |
| DE | 19959366 | 6/2001 |
| DE | 10340059 | 2/2005 |
| DE | 69636845 | 8/2007 |
| DE | 102006036020 | 2/2008 |
| DE | 102008054138 | 5/2010 |
| EP | 0015599 A1 | 9/1980 |
| EP | 1062916 | 12/2000 |
| EP | 1547543 | 6/2005 |
| EP | 2039320 | 3/2009 |
| KR | 10-2007-0009060 | 1/2007 |
| WO | WO 97/43977 | 11/1997 |
| WO | WO 99/52466 | 10/1999 |
| WO | WO 02/26154 | 4/2002 |
| WO | WO 2004/008983 | 1/2004 |
| WO | WO 2004/073541 | 9/2004 |
| WO | WO 2004/080328 | 9/2004 |
| WO | WO 2006/109176 | 10/2006 |
| WO | WO 2008/011948 A1 | 1/2008 |
| WO | WO 2010/049135 | 5/2010 |

OTHER PUBLICATIONS

Official Action for U.S. Appl. No. 13/982,799, mailed Jul. 30, 2014, 11 pages.
International Search Report prepared by the European Patent Office on Jul. 31, 2007, for International Application No. PCT/EP2007/003480; Applicant, Holger Zipprich.
Written Opinion for International (PCT) Application No. PCT/EP2007/003480, mailed Apr. 20, 2007.
International Preliminary Report on Patentability prepared by the International Preliminary Examining Authority for International Application No. PCT/EP2007/003480 and English translation.
International Search Report prepared by the European Patent Office on Aug. 18, 2011 for International Application No. PCT/EP2011/002229.
International Search Report prepared by the European Patent Office on May 14, 2012, for International Application No. PCT/EP2012/000413.

(56) References Cited

OTHER PUBLICATIONS

Official Action for U.S. Appl. No. 12/297,570 mailed Apr. 11, 2011, 15 pages.
Official Action for U.S. Appl. No. 12/297,570 mailed Jan. 5, 2012, 9 pages.
Official Action for U.S. Appl. No. 12/297,570 mailed Jan. 3, 2013, 18 pages.
Official Action for U.S. Appl. No. 12/297,570 mailed May 31, 2013, 18 pages.
Official Action for U.S. Appl. No. 13/696,162 mailed Apr. 12, 2013, 15 pages.
Official Action for U.S. Appl. No. 13/696,162 mailed Feb. 24, 2014, 15 pages.
International Search Report and Written Opinion prepared by the European Patent Office on Mar. 14, 2012, for International Application No. PCT/EP2011/005748.
International Search Report prepared by the European Patent Office on Jul. 30, 2012, for International Application No. PCT/EP2012/001220.
Official Action with English Translation for China Patent Application No. 201280012017.8, dated Jun. 23, 2015, 12 pages.
Official Action for U.S. Appl. No. 14/003,917, mailed Jun. 30, 2014 8 pages.
Official Action for U.S. Appl. No. 14/003,917, mailed Jan. 15, 2015 8 pages.
Official Action for U.S. Appl. No. 13/696,162, mailed May 6, 2015 12 pages.
Official Action for U.S. Appl. No. 13/982,799, mailed Mar. 3, 2015 7 pages.
Official Action for German Patent Application No. 102006018726.1, dated Jun. 24, 2015, 6 pages.
Official Action with English Translation for China Patent Application No. 201180062921.5, dated May 13, 2015, 13 pages.
Official Action with English Translation for China Patent Application No. 201280010689.5, dated Jul. 20, 2015, 11 pages.
Official Action for U.S. Appl. No. 14/003,917, mailed Mar. 29, 2016 8 pages.
Official Action for U.S. Appl. No. 12/297,570, mailed Mar. 22, 2016 15 pages.
Official Action for U.S. Appl. No. 13/696,162, mailed Nov. 20, 2015 13 pages.
Official Action for U.S. Appl. No. 13/696,162, mailed Jun. 3, 2016 14 pages.
Official Action for U.S. Appl. No. 13/982,799, mailed Oct. 8, 2015 8 pages.
Notice of Allowance for U.S. Appl. No. 13/982,799, mailed Mar. 15, 2016 6 pages.
Official Action for U.S. Appl. No. 14/003,917, mailed Oct. 7, 2016 7 pages.
Official Action for U.S. Appl. No. 12/297,570, mailed Oct. 26, 2016 14 pages.
Notice of Allowance for U.S. Appl. No. 13/696,162, mailed Sep. 2, 2016 5 pages.
Official Action with English Translation for China Patent Application No. 201280012017.8, dated Nov. 29, 2016, 12 pages.

* cited by examiner

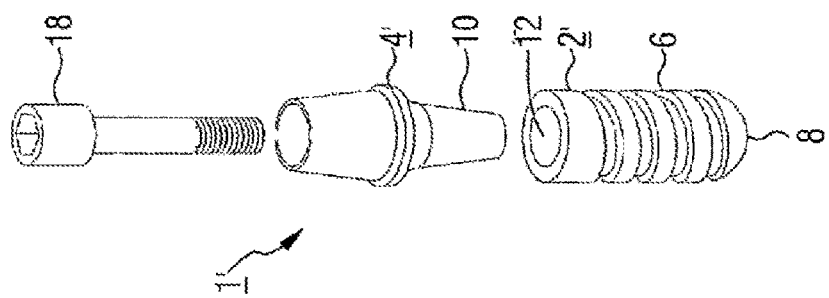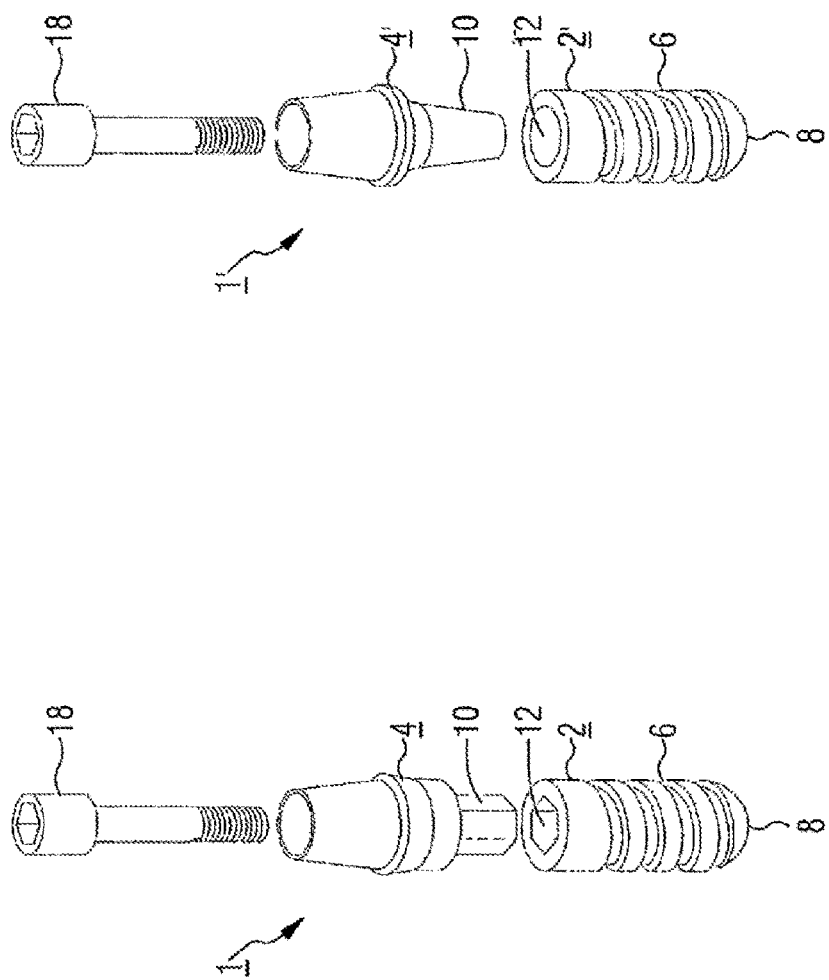

DENTAL IMPLANT SYSTEM AND METHOD FOR PRODUCING A DENTAL IMPLANT SYSTEM

CROSS REFERENCE TO RELATED APPLICATIONS

This application is a national stage application under 35 U.S.C. 371 and claims the benefit of PCT Application No. PCT/EP2011/005748 having an international filing date of Nov. 15, 2011, which designated the United States, and which PCT application claimed the benefit of German Patent Application No. 102010051176.5 filed Nov. 15, 2010, the disclosure of which is incorporated herein by reference.

The invention relates to a dental implant system comprising a first implant part, provided for introduction into a jawbone, and comprising a second implant part associated therewith, provided for attaching a tooth replacement part, the implant parts being mechanically interconnectable via a connection pin which is integrally formed on one of the implant parts and which is insertable into a receiving duct provided in the other implant part.

In the context of reconstructive treatment, dental implants may be used to compensate the loss of a tooth. They are conventionally inserted into the jawbone, in place of a tooth which has been extracted or has fallen out, where after a healing phase of approximately four to twelve weeks they hold a prosthetic part or a crown, which acts as a tooth replacement. For this purpose, a dental implant of this type is conventionally in the form of a suitably formed metal body, which is inserted into the jawbone by screwing in at the provided place. At the apical end, the dental implant thus generally comprises a predominantly self-cutting screw thread, with which the dental implant is inserted into the correspondingly prepared implant bed.

So as to enable facilitated introduction into the patient's mouth, and in particular an especially extensive preparation of the actual prosthesis during attachment to the implant even prior to treating the patient, for example in a dental laboratory, dental implant systems may be formed in a plurality of parts. In particular, in this context a construction which is basically in two parts may be provided, the dental implant system comprising a first implant part, provided for introduction into the jawbone, also known as the actual implant or the post part, and in addition thereto an associated second implant part, also known as the structural part, to which the tooth replacement part provided as a prosthesis or the like can in turn be attached. The first implant part or post part is conventionally provided with a thread on the outside thereof, which may be in the form of a self-cutting thread or a non-self-cutting thread. The post part is conventionally anchored in a correspondingly prepared implant bed of the jawbone. In this context, the construction of the thread provided in the outer region of the dental implant is conventionally configured for a high primary stability of the arrangement and for uniform transmission of the forces occurring in the jawbone the dental implant is loaded during chewing.

A connection pin which is integrally formed on one of the implant parts, generally on the structural part, is conventionally provided for mechanically interconnecting the implant parts. It can be inserted into a receiving duct which is provided in the other implant part, generally in the post part. In this context, the connection pin, on the one hand, and the receiving duct, on the other hand, are generally adapted to one another in terms of shape selection and dimensioning, in particular of the cross-sections, in such a way that whilst assembly is comparatively simple it is still possible to achieve good guidance of the components inside one another and thus sufficiently high mechanical stability. The structural part, the upper region of which is conventionally equipped with a crown, another prosthetic provision or the like in a manner known per se, can thus be glued to the post part via the connection pin which is inserted into the receiving duct, for mechanical connection to the post part. However, the structural part can also be pressed into the post part and merely be fixed by jamming, or else additionally be fixed by way of cementing or gluing.

However, in implant systems of this type, the dental implant is loaded extremely heavily when the structural part is screwed in, and also in particular during subsequent chewing processes, in such a way that an adhesive connection of the aforementioned type does not have sufficiently high mechanical stability, simply in view of the very long dwell time in the patient's mouth. So as to accommodate this, the structural part may also alternatively be screwed to the post part via a suitably selected connecting screw. In this context, during the introduction the thread of the connecting screw is conventionally screwed into an associated internal thread in the post part. In this context, the screw head of the connecting screw presses the structural part onto the dental implant during screwing in, by depressing said structural part. Multi-part dental implant systems of this type, comprising a screw connection between the structural part and the post part, are known for example from DE 10 2006 018 726 A1 and DE 10 2008 054 138 A1.

The first implant part or post part, and likewise the second implant part or head part or structural part, conventionally consist of a suitably selected metal, in particular of titanium or a titanium alloy. By way of this material selection, an adequate acceptability for the patient and good biocompatibility can be achieved. In addition, implant systems manufactured on this material basis have a high long-term stability and a low susceptibility to fracturing. Accordingly, titanium is widespread as a base material for implant systems and also enjoys extensive scientific acceptance, and in particular the sterilisation required for use within reconstructive treatment can also be ensured comparatively simply and reliably. The material costs are also limited, in such a way that even comparatively large numbers of implant systems can generally be produced on this basis at reasonable expense.

On the other hand, however, in metal-based implant systems of this type, allergenic potential under some circumstances cannot be excluded. Metal allergies are generally brought about by the formation of metal ions. There is further the risk that particles which split off from the implant, for example by flaking off from the implant surface or by abrasion in multi-part systems, may induce inflammatory reactions in the patient's mouth. In addition, the inherent colour of the metal implant components may have an aesthetically and/or visually objectionable impact, and the electrical conductively of the metal components can lead to objectionable effects.

For these reasons, a metal-free configuration of implant systems may be desirable. Ceramic materials in particular, conventionally based on zirconium oxide (preferably stabilised with yttrium oxide or aluminium oxide), or else zirconium alloys, zirconium oxide aluminium oxide ceramic materials, or ceramic materials which contain either zirconium oxide or aluminium oxide or comprise at least one of the ceramic materials as a primary component, come into consideration as an alternative to metal systems as the base material for implants. Further, ceramic materials formed on the basis of silicon or silicon oxide and containing for example admixtures of nitrogen, hydrogen, carbon or tungsten may be used. Ceramic material implant systems have the general advantage of higher biocompatibility and thus good acceptability, the allergenic potential being markedly low. The surface is highly unfavourable for bacterial growth, in such a way that implants of this type are particularly favourable as a whole for long-term applications and high dwell times in the patient's mouth. In addition, virtually no grey discolorations occur in the surrounding tissue, in such a way that particularly high-quality aesthetic effects can be achieved.

However, dental implants based on ceramic material are currently basically only known in a single-part configuration. The material properties of the ceramic material components (for example brittleness, high hardness, little or no ductility) make assembly more difficult and make high durability and long-term stability of implant systems formed in a plurality of parts virtually impossible. Specifically, in particular because of the low resilient deformation and lack of plastic deformation of ceramic materials, in particular at (Vickers) material hardnesses of more than 500 or even of more than 1000, planar contact between the components can only be achieved with great difficulty, in such a way that point loads can occur in the contact region of the implant parts of multi-part systems, in particular when the comparatively large chewing forces are transmitted. These point loads can in turn lead to increased local pressure in the connection region, and consequently to the potential formation of microfissures or damage in the ceramic material structure, which in turn can lead to fractures or breaks in the components themselves. It is therefore only possible to exploit the basic advantages of multi-part dental implant systems to a very limited extent in ceramic-based systems.

The object of the invention is therefore to provide an implant system of the aforementioned type—preferably formed in two or more parts—which makes particularly high stability and a long duration of use possible, even when ceramic base materials, or base materials comparable therewith in terms of the basic material properties thereof, are used for at least one of the implant parts. Further, a particularly suitable production method for the implant system is to be provided.

As regards the implant system, this object is achieved according to the invention by the features of claim 1. In this context, the connection pin is formed of a material having a hardness of at least 500, preferably of at least 750, particularly preferably of at least 1000, and comprises, in a contact region with the receiving duct on the surface thereof, a coating, preferably in the form of a spacer, formed of a material softer than the material of the connection pin, in particular having a hardness of at most 25, preferably of at most 20, particularly preferably at most 15. In this context, to produce a material fit connection to the coating, the connection pin is made porous in the surface region thereof which is provided with the coating, preferably having a porosity of at least 0.1. In this context, the aforementioned hardnesses should be interpreted as DIN Vickers hardnesses based on a 10 kilopond testing force, that is to say the aforementioned hardness of 500 for example corresponds to a standardised specification of 500 HV 10.

Advantageous embodiments of the invention form the subject-matter of the dependent claims.

The invention is based on the consideration that, in multi-part implant systems, high stability and long life can be achieved if the forces which occur in particular during chewing processes are accommodated in a suitable manner. In particular when these forces are transmitted from the structural part into the post part anchored in the jawbone, in multi-part dental implant systems, a force transmission which is very gentle to the materials should be ensured. This can be achieved in particular in that planar contact is consistently produced while largely preventing localised contact points between the implant parts. Unlike metal-based systems, in which planar contact of this type sets in virtually automatically as a result of the higher resilient deformation and the ductility of the material under the applied forces, the planar contact in ceramic-based systems could only be insufficient, because of the lack of ductility of the material and in view of the virtually unavoidable manufacturing tolerances and imprecisions.

So as to counteract this in a suitable manner, an additional element is now provided in the construction of the dental implant system, and is intended to prevent the formation of localised points of contact between the implant parts in the manner of an equalising body. The spacer provided for this purpose should be configured in such a way, in terms of the material selection thereof, that as a result of a suitable ductility it produces a suitable equalisation in the intermediate space between the implant parts and thus ensures planar force transmission between the components. For this purpose, the material of the spacer should be selected to be correspondingly softer and thus more deformable than the material of the actual implant parts.

The spacer could in principle be in the form of a meshwork of material threads, which are in turn connected to the connection pin in a material fit, thus for example glued on or melted on, in such a way that it is in particular in the form of a net-like coating. In this way, on the one hand it is possible to set a suitable minimum distance between the contact faces, which compensates the surface roughness of the contact faces which may be caused during manufacture, whilst on the other hand free volumes suitable for receiving material are still formed in the intermediate spaces formed by the tissue threads. These volumes are particularly suitable for receiving excess material, for example glue or the like. A spacer formed in this manner, also considered to be a spacer according to the invention, is thus particularly suitable for gluing the implant parts together.

Now, however, the spacer is in the form of a coating applied to the surface of the connection pin. The coating may be applied to the surface of the connection pin in part, or in the manner of a net, but is preferably formed continuously over the whole surface. This results in the spacer being formed over the whole surface of the connection pin. In a configuration of this type, the spacer is equally suitable both for gluing the implant parts together and for producing a connection by screwing, since in this case the spacer can still bring about damping during the force transmission between the implant parts which are screwed together.

In this context, for good workability, the spacer is connected to the connection pin in a positive fit, that is to say in particular as a coating or a glued-on or melted-on element. Analogously, the spacer may of course also be applied to the inside of the receiving duct in the manner of an internal coating, in such a way that it is positioned between the implant parts in the interconnection region of the implant parts even after they are assembled. Further, a combination of two spacers, that is to say one on each of the two implant parts, is also possible.

So as to ensure reliable positioning of the coating forming the spacer, as well as particularly high long-term stability and reliable adhesion of the coating, even during assembly with comparatively high pressing forces and a short assembly time, the material fit connection of the spacer to the connection pin (or, in an analogous configuration, the inner surface of the receiving duct) is made particularly close. For this purpose, the connection pin comprises a roughened and/or porous surface in the region of the connection thereof to the spacer or in the region of the coating. The porosity of the surface, produced in particular by roughening, is thus configured in such a way that a porous surface is provided precisely in the region of the material fit connection of the connection pin to the coating, preferably having a porosity with a structural size of at most one micrometer, alternatively or additionally preferably having a porosity of at least 0.1. A porously formed surface of this type ensures that, in particular in combination with a suitable material selection for the coating, the material thereof can penetrate at least in part into the cavities in the surface, which are present as a result of the porosity, and there is thus a particularly close material fit connection. The porosity, given as 0.1, was determined using the following formula:

$$\Phi = 1 - \frac{\rho}{\rho_0}$$

In this context, the Greek letters used therein represent: $\Phi$=porosity, $\rho$=bulk density, $\rho_0$=true density.

Porosity is thus a dimensionless measurement. It is the ratio of the cavity volume to the total volume of a material or mixture of materials, and is defined as 1 minus the quotient of the bulk density of a solid body and the true density.

In this context, the roughening is advantageously applied to the surface after the actual production, that is to say in particular in an additional treatment step. In this context, the surface of the connection pin in the region of the material fit connection to the spacer generally advantageously has an $r_a$ value of at most 10%, preferably at most 5%, of the layer thickness of the coating or spacer. In other words, the average roughness of the surface is advantageously at most 10% of the layer thickness of the coating or of the spacer. The roughening may for example be carried out mechanically (for example by blasting such as sandblasting), chemically (for example by etching) or by laser irradiation, preferably with a femtosecond laser. In this context, in particular by using laser irradiation, preferably using a laser having a pulse duration of less than for example 1 ps, targeted structures or structural patterns can also be applied to the surface to be coated, it additionally being possible to prevent deeper damage to the underlying material, that is to say in particular the ceramic material.

So as to make reliable mechanical connection possible between the implant parts with greater tightness, the cross-section of the connection pin advantageously has an outer contour adapted to the contour of the associated receiving duct. As seen in the longitudinal direction of the connection pin or receiving duct, the two may additionally be configured with a constant cross-section, that is to say for example with a cylindrical base body. Advantageously, however, the cross-sections taper towards the free end of the connection pin, in a particularly advantageous embodiment in a conical configuration, in such a way that a good non-positive fit can be achieved with high tightness in a particularly simple manner. In a further advantageous embodiment, the outer contour of the connection pin—and the inner contour of the receiving duct adapted correspondingly thereto—have a cross-section having multiple symmetry in part or in portions. In this way, on the one hand a reliable rotary alignment of the structural part can be achieved during assembly, that is to say during the introduction into the patient's mouth, in the manner of indexing, whilst on the other hand, even when introducing high torques into the system, the selected rotary alignment in the tooth environment is reliably maintained, in the manner of a rotary lock.

As regards the layer thickness thereof, the spacer is advantageously dimensioned in such a way that, on the one hand, excessive flexibility and deformation of the whole assembled system as a result of an excessive layer thickness are prevented and, on the other hand, reliable compensation of surface roughness and manufacturing tolerances is ensured. In this context, it is preferably also taken into account that, in particular with conical connections between the structural part and the post part, the resilient deformation of the post part is used to compensate angle tolerances in the cone angle resulting from manufacture. In conventional, metal multi-part implant systems, the angle tolerances in this context are conventionally dimensioned in such a way that the cone angle of the shaped recess in the post part is smaller than the cone angle of the contact pin integrally formed on the structural part.

In screw systems, the wall of the post part thus deforms in the resilient region when the connecting screw is tightened, in such a way that the contact faces end up in planar contact with one another. Since this is not possible in ceramic materials because of the lack of deformation and the high (Vickers) hardness (HV) thereof, for example more than 500 or even more than 1000, the coating provided as a spacer should make these compensations possible. For the aforementioned reasons, in an advantageous embodiment, as regards otherwise conventional dimensioning parameters of the dental implant systems (total length, diameter of the post part etc.), a layer thickness is provided of at least 0.001 mm, preferably at least 0.05 mm, particularly preferably at least 0.01 mm and/or of at most 0.3 mm, preferably at most 0.2 mm, particularly preferably at most 0.1 mm.

As regards material selection, the respective components, in particular the implant parts, are advantageously suitably selected with a view to a high long-term stability, in particular in the provided field of use, and also with a view to particularly high acceptability and biocompatibility. In this context, for example a suitably selected metal, preferably gold, which is sufficiently soft in particular as regards the material selection of the actual implant parts, may be selected for the spacer. However, so as also to make a completely metal-free configuration of the implant system possible, in a particularly advantageous embodiment the spacer is produced from a plastics material, preferably from a thermoplastic material having a high load capacity from the group of polyetherketones, in particular from polyetheretherketone, also known as PEEK. PEEK conventionally has a Vickers hardness of approximately 12, and thus meets the configuration criterion which is now provided in a particularly satisfactory manner.

In an additional or alternative advantageous development, the plastics material forming the spacer has a modulus of elasticity of approximately 1000 MPa. The spacer is thus sufficiently hard to withstand the forces which occur during chewing, in such a way that plastic deformation and "swelling" of the material are prevented.

So as reliably to prevent the material from swelling after introduction into the patient's mouth, and in particular reliably to prevent the formation of fissures in the implant parts which may result from swelling of this type, the plastics material which forms the spacer may, in an additional or alternative advantageous embodiment, have a water absorption of at most 1%, preferably of at most 0.5%, particularly preferably of at most 0.2%.

With a view to the rules and regulations which are generally conventional in therapeutic patient care, the components of the implant system are advantageously configured for the possibility of problem-free sterilisation. For this purpose, the plastics material forming the spacer advantageously has a softening point of at least 140° C., preferably of at least 160° C., particularly preferably of 300° C., in such a way that conventional superheated steam sterilisation (usually at a temperature of 134° C.) can be carried out once or else a plurality of times as required, without limitations.

The connection pin is preferably formed from a ceramic material, in particular from zirconium oxide, in such a way that high stability of the system is ensured overall. A ceramic material connection pin of this type comprising an applied surface coating is particularly advantageous for use in combination with a post part or receiving duct made of titanium or another metal material, since in principle, with the ceramic material/metal material pairing, in particular ceramic material/titanium, metal wear and corresponding surface and colour alterations have to be anticipated as a matter of basic principle, as a result of the greater hardness of the ceramic material. The aforementioned ceramic material conventionally has a Vickers hardness (HV) of more than 1000. Since the aforementioned effects already occur strongly in ceramic materials having a Vickers hardness of 500 or more, this is already sufficient to make the spacer provided as an intermediate or buffer element particularly advantageous. The aforementioned effects, in particular the surface wear, can be prevented particularly effectively by way of the surface coating, which acts as a spacer between the ceramic material on the one hand and the metal, in particular titanium, on the other hand.

However, in a particularly advantageous embodiment, a ceramic material, in particular zirconium oxide or aluminium oxide, is used for the implant parts as a whole, or in any case as a main component, resulting in a metal-free base body being provided. Materials of this type are distinguished by the excellent biocompatibility thereof and provide a bacteria-resistant surface. In this context, in a particularly advantageous embodiment, the connection pin is made of zirconium oxide stabilised with yttrium oxide and/or aluminium oxide, the surface of the connection pin, in a further advantageous embodiment, comprising a reinforcement zone, having a reduced yttrium oxide or aluminium oxide content by comparison with the internal volume of the connection pin, in the region of the material fit connection to the spacer.

To produce a reinforcement zone of this type, a ceramic material base body may preferably be treated by way of laser treatment and/or in a liquid and/or gaseous medium, preferably in an acid bath, the acid bath being displaced with ions which each consist of an element from one of main groups V to VII of the periodic table of elements or comprise an element of this type as a component. By way of this treatment, a ceramic material body can be obtained in which, in a surface region, there is a reinforcement region by comparison with the internal volume in terms of a structural parameter, in particular an alloyed component or a crystallographic phase content.

As has completely surprisingly and unexpectedly been found, this very method leads to the formation of surface structures which ensure particularly favourable wetting properties and make possible particularly good adhesion of the coating provided as a spacer when the ceramic material body is used as a carrying body for the spacer.

Specifically, as a result of the treatment of the ceramic material base body by way of etching, and in particular intercrystalline etching, a specific nanostructure is formed on the surface. In this context, a plurality of comparatively small pores or depressions will be encountered, having an average extent in the sub-micrometer range, preferably less than 500 nm and in particular less than 250 nm. Structures of this type may for example be detected using electron microscope images. The surface is distinguished in particular in that the depth of the nanostructure, that is to say the depth of the pores which can be achieved in this context, is greater than the structural width, that is to say the characteristic lateral extent of the structures which are achieved. The provided porosity of the surface can thus be provided with properties which are particularly favourable for the desired material fit connection having a high load capacity.

The ratio between the structural depth and the structural width in the nanostructure is greater than 1:1, advantageously greater than 1.5:1 and in particular greater than 2:1.

The reinforcement zone which may advantageously be provided in the surface region, and which ultimately brings about the desired structure and the desired properties for the connection to the material of the spacer, can be produced in particular by selective or at least selectively accelerated dissolution of individual components, such as chemical elements and/or oxides, from the surface, preferably by way of a suitably selected etching process. Favourable structures of this type may in particular be created in that individual elements and/or individual metal oxides found in the ceramic material (zirconium oxide, aluminium oxide, yttrium oxide, hafnium oxide etc.), in particular yttrium oxide and hafnium oxide, are dissolved from the surface. This results in a reinforcement region of these metal oxides on and/or in the region adjacent to the surface.

Further, during analysis with regard to the phase properties, it has been shown that the ratio between the tetragonal and monocline phases in the stabilised zirconium oxide was altered on the surface by way of one of the above-disclosed treatments. After the sintering process, by way of a method of this type the monocline phase in the surface could be increased or reduced to or by at least 0.1%, preferably to or by more than 0.5% and in particular to or by more than 1.5%. Since the surface is placed under pressure as a result of the lower density of the monocline phase, this inhibits the initial fissure formation, in such a way that an increase in the initial strength can be anticipated.

The production of the provided reinforcement region in the surface of the ceramic material body can in particular take place by way of an etching process in a suitably selected acid bath. In this context, the provided reaction partners for the ceramic material of the base body, that is to say the ions comprising components from main groups V to VII of the periodic table of elements, may in particular act to form salts with the respective metal. In particular, the acid bath may comprise ions which consist of the elements of nitrogen (N), oxygen (O), fluorine (F), chlorine (Cl), sulphur (S) and/or phosphorus (P), or which comprise them as components. During treatment in the acid bath, there is the possibility that the ions of the acid will chemically alter the surface and be left behind on the surface as an impurity.

As regards the method for producing a dental implant system of this type, the aforementioned object is achieved in that the surface of the connection pin is roughened in the region of the provided connection to the spacer before the material fit connection to the spacer is produced.

In this context, in an advantageous embodiment, the roughening may be provided by laser irradiation or by sandblasting. However, it is particularly advantageous if the surface of the connection pin is made porous in the region of the provided connection to the spacer, preferably by way of an etching process, before the material fit connection to the spacer is produced.

To apply a coating, provided for forming the spacer, to the connection pin, a dispersion is advantageously applied to said connection pin and subsequently dried. The dispersion advantageously comprises particles in solution, provided to form the coating, having a particle size of up to 20 µm. In this case, the dispersion may be sprayed on or else applied in some other suitable manner, it advantageously being possible for a drying step to be carried out subsequently at a drying temperature of for example approximately 150° C. As a result, the solvent components are volatilised, in such a way that the material particles precipitate and thus form the coating. In this context, the drying preferably takes place in a vacuum or under negative pressure, in such a way that the formation of air inclusions is kept particularly low. In particular because air inclusions of this type can block the entry of the material into the surface pores of the carrying body, this particularly promotes a close material fit connection.

In a further advantageous embodiment, preferably after drying, the connection pin provided with the coating is additionally heat-treated at a temperature above the softening point of the coating material, preferably of at least 350° C., particularly preferably of at least 400° C. In this way, homogenisation can be provided in the manner of melting on the applied material, penetration of the coating material into the surface pores or surface roughness in the connection pin potentially being promoted at the same time. Treatment of this type is particularly favourable and effective for layer thicknesses of up to approximately 0.1 mm. Alternatively, for layer thicknesses greater than 0.1 mm, a powder coating could also be provided.

The advantages achieved by the invention are in particular that, as a result of the spacer provided in the connection region of the connection pin and the receiving duct, imprecisions and manufacturing tolerances in the components can be compensated, in such a way that even when ceramic materials are used for the connection pin or even the implant parts, planar contact between these parts can be produced overall. As a result, it is possible for the forces to be transmitted reliably in a manner which is gentle to the materials, even with regard to the high chewing forces which occur, in such a way that it is made possible to use the inherently desirable ceramic materials even in multi-part dental implant systems.

A porosity of at least 0.1, provided in the surface region, is also particularly advantageous in other fields of use of ceramic materials, in particular based on zirconium oxide, so as to be able to apply an adhesive coating made of a plastics material, in particular PEEK. The advantages of a coating based on plastics material on a ceramic base body are in particular the alteration to the chemical properties and in particular the acid resistance. As regards the alterations to the mechanical properties, the optimised force introduction/force transmission are particularly noteworthy. However, the alteration to the coefficient of friction µ by way of an adhesive coating provides ceramic materials with major advantages in terms of applicability, in particular by comparison with other metal materials.

An embodiment of the invention is described in greater detail with reference to the drawings, in which:

FIGS. 1 to 3 are each an exploded view of a dental implant system,

Figure 5:
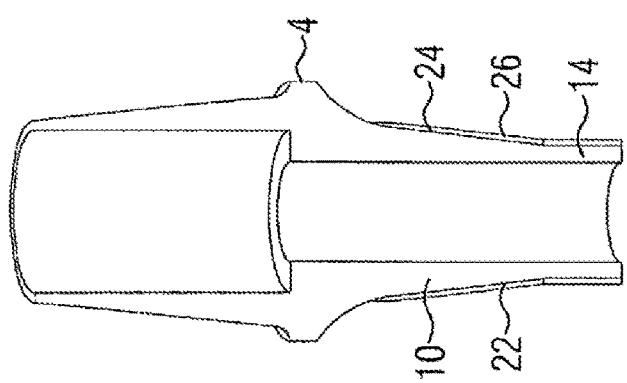
Figure 11:
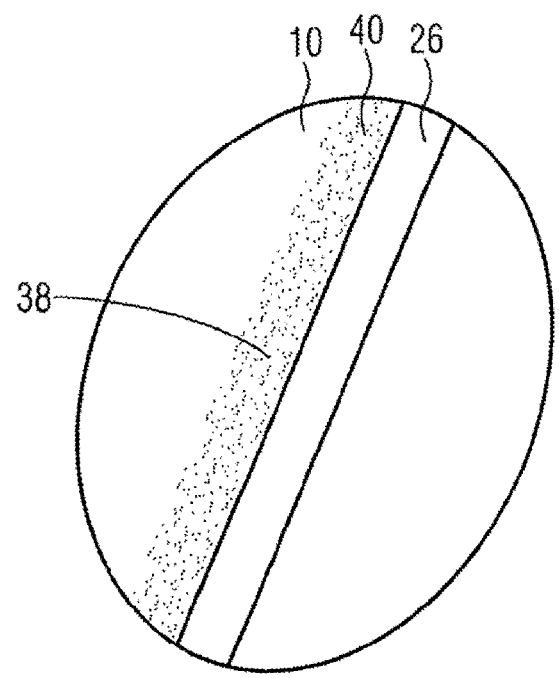

FIG. 5 is a cross-section of a structural part of the dental implant system of FIGS. 1 to 3, FIG. 6 is a cross-section of a post part of the dental implant system of FIGS. 1 to 3, FIGS. 7 and 8 are a side view of a structural part of the dental implant system of FIGS. 1 to 3, FIG. 9, 10 each show an alternative embodiment of a dental implant system, and FIG. 11 is a detail of the connection region of the components of the dental implant system.

Like components are provided with like reference numerals throughout the drawings.

The dental implant system 1, 1', 1" in accordance with FIGS. 1 to 4 is in each case provided for use in the jawbone in place of a tooth which has been extracted or has fallen out, so as to hold a prosthetic part or crown there which acts as a tooth replacement. For this purpose, the dental implant system 1, 1', 1" is in each case formed in a plurality of parts, and comprises a first implant part 2, 2', 2" in the form of what is known as a post part and a second implant part 4 associated therewith, also known as a structural part and provided for attaching a tooth replacement part. In this context, the first implant part 2, 2', 2" or post part is provided with an external thread 6 on the outside thereof, which is in particular in the form of a self-cutting screw thread on the apical end 8. In this way, the first implant part 2, 2', 2" or post part can be inserted into the jawbone at the provided place by being screwed in.

So as to make introduction into the post part or first implant part 2, 2', 2" possible with high mechanical stability after the tooth replacement part or the prosthesis has been suitably applied to the structural component or second implant part 4, a connection pin 10 is formed integrally on the second implant part 4, and can be inserted into an associated receiving duct 12 which is provided in the first implant part 2, 2', 2". Inserting the connection pin 10 into the receiving duct 12 results in mechanical interconnection of the implant parts 2, 4. In this context, for high mechanical stability, the outer contour of the connection pin 10 is adapted to the inner contour of the receiving duct 12, it being possible for the two to be formed conically as seen in the longitudinal direction (embodiment in accordance with FIG. 2). In addition, as is provided in particular in the embodiment in accordance with FIG. 1, the outer contour of the connection pin 10—and the inner contour of the receiving duct 12 adapted correspondingly thereto—may have a cross-section having multiple symmetry (in the embodiment six-way symmetry), in such a way that when the aforementioned components are assembled, a rotary lock is produced, and thus a reliable rotary alignment of the structural part with respect to the post part can be set. In the embodiment in accordance with FIGS. 3 and 4, an index or an indexing element 14, in turn having a cross-section having multiple symmetry, is arranged on the end of the connection pin 10 to form a rotary lock for this purpose, and engages in a corresponding, associated duct end piece 16 in the receiving duct 12 when assembled.

The dental implant systems 1, 1', 1" in the embodiments in accordance with FIGS. 1 to 4 are each configured for interconnecting the implant parts 2, 4 by screwing. A connecting screw 18 is provided for this purpose in each case, and engages in a screw thread 20 which is provided inside the first implant part 2, 2', 2" in each case.

In terms of the material selection thereof, the implant parts 2, 4 are adapted suitably to the purpose of use, and may in principle be made of ceramic material such as zirconium oxide or aluminium oxide. In particular zirconium oxide stabilised with yttrium is selected as the material for the connection pin 10. This has a comparatively high Vickers hardness (HV) of 1500±100. However, because of the low resilient deformation and lack of plastic deformation of a material which is this hard, it should be assumed that there is no planar contact between the implant parts 2, 4 in the region of the connection pin 10. Thus, in particular when the comparatively large chewing forces are transmitted, point loads may occur in the contact region of the implant parts 2, 4. These could in turn result in increased local pressure in the connection region and consequently in the potential formation of microfissures or damage in the ceramic material structure, which could in turn lead to fractures or breaks in the components themselves. Further—in particular with a combination of a ceramic material connection pin 10 with a metal post part 4—metal wear could occur on the post part because of the large difference in hardness between the components, and could lead to undesirable impurities and/or discolorations or the like.

So as to counteract this in a suitable manner, as an additional element in the construction of the dental implant system 1, 1', 1" in the manner of a compensating body or spacer 22, the connection pin 10 is provided with a coating 26 on the surface 24 thereof in a contact region with the receiving duct 12, as is shown in the cross-sectional drawing in accordance with FIG. 5. In this context, it is provided as a configuration criterion for the coating 26 that it should be formed of a material, having a (Vickers) hardness of at most 25, which is much softer than the material of the connection pin 10. As a result, by virtue of a suitable ductility, the coating 26 produces suitable compensation in the intermediate space between the implant parts 2, 4, in such a way that planar force transmission is ensured between the components. In the embodiment, the coating 26 is produced from a plastics material, specifically from the thermoplastic material polyetheretherketone, also known as PEEK, which has a high load capacity. PEEK conventionally has a Vickers hardness of approximately 12, and thus meets the configuration criterion which is now provided in a particularly satisfactory manner.

Figure 3:
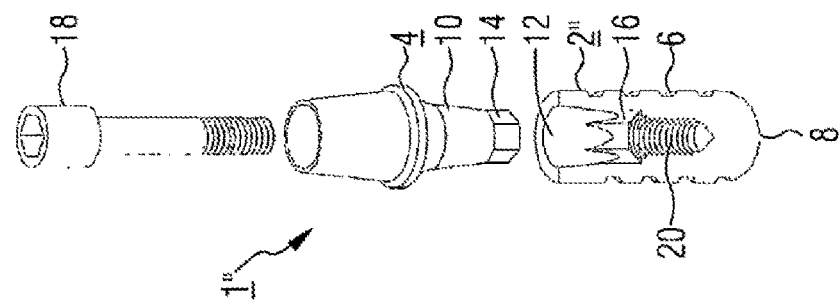
Figure 4:
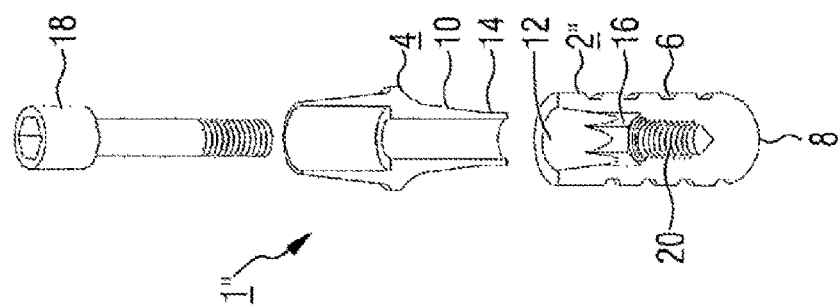
FIG. 4 is a longitudinal section of the dental implant system of FIG. 3.
Figure 6:
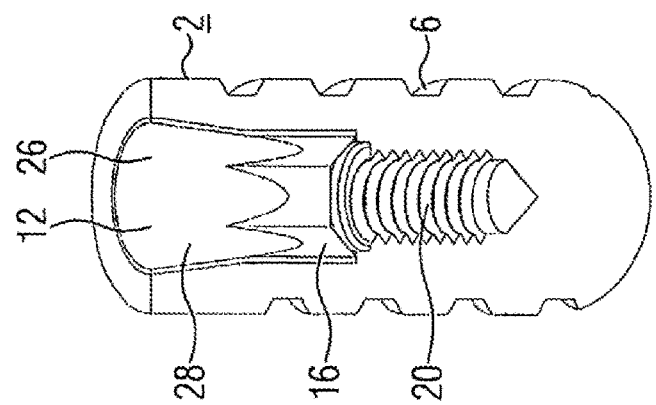

Naturally, with the same effect, the coating 26 may also alternatively or additionally be arranged on the inner surface 28 of the receiving duct 12 in the post part 2 or second implant part 4, as is shown in the cross-sectional drawing of FIG. 6.

Figure 8:
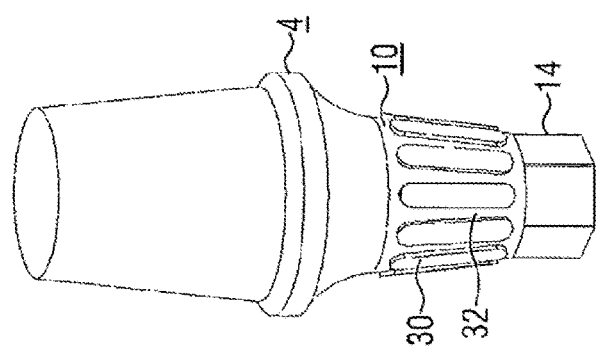
Figure 7:
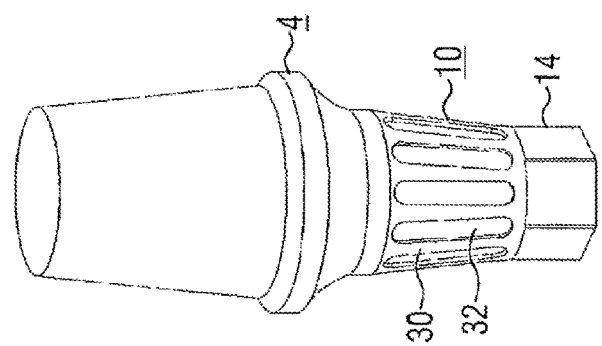
Figure 10:
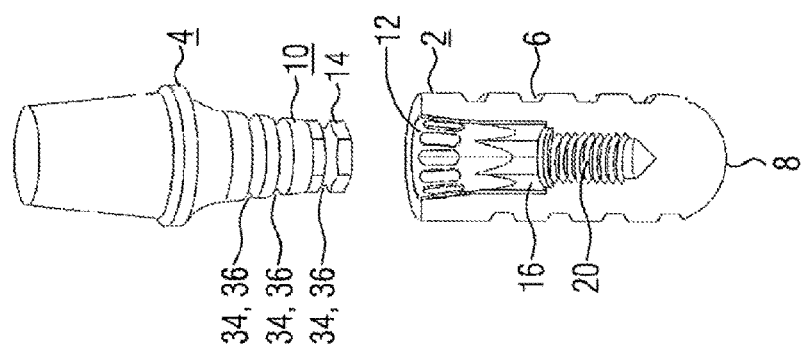
Figure 9:
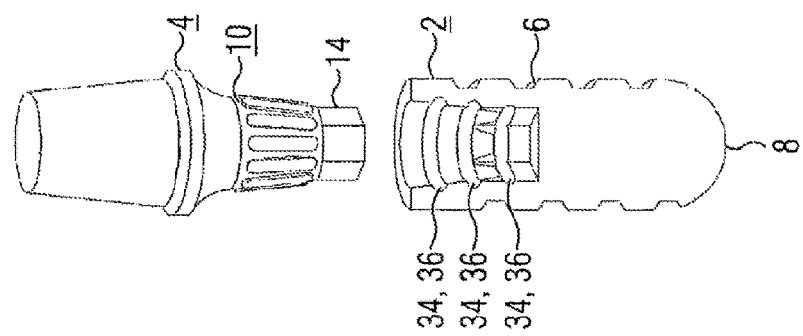

Preferably, the coating 26 which is provided to form the spacer 22 is formed continuously in the manner of a coating over the whole surface. Alternatively, however, in the manner of a net, mesh or the like which encloses the connection pin 10, it may also comprise a plurality of sub-elements or sub-coatings 30a, b, which are each connected in a material fit to the connection pin 10—or if applied on the inside to the inner surface of the receiving duct 12—so as to form intermediate spaces 32a, b, as a net-like formation (FIG. 7) or else mutually independently (FIG. 8). In this way, on the one hand the sub-elements or sub-coatings 30a, b, make it possible to set reliably a suitable minimum distance between the contact faces, which compensates the surface roughness of the contact faces which may occur as a result of manufacture, whilst on the other hand free volumes suitable for receiving material are still formed in the intermediate spaces 32a, b. These volumes are particularly suitable for receiving excess material, for example glue or the like. A connection system which is formed in this manner is thus particularly suitable for adhesive interconnection of the implant parts 2, 4. This formation of receiving chambers for excess glue can be promoted even more strongly in that further receiving chambers 34, in the embodiment of FIGS. 9 and 10 in the form of additionally applied circumferential grooves 36, are provided mechanically in the respective other component—shown in FIG. 9 for the receiving duct 12 and in FIG. 10 for the connection pin 10.

In the two preferred variants, that is to say both in a configuration as a continuous coating 26 over the entire surface and in a configuration comprising intermediate spaces 32a, b, a close material fit connection is provided between the connection pin 10 or inner surface 28 of the receiving duct 12, on the one hand, and the coating 26 which forms the spacer 22, on the other hand. So as to promote this particularly strongly, in this context the surface of the connection pin 10 is configured to be roughened and/or porous in the region of the coating. As is shown schematically in the enlarged detail in FIG. 11, the roughening or porosity in the surface region, in particular of the respective ceramic material component, leads to a plurality of small material chambers 38 being formed, into which the comparatively soft material forming the coating 26 can penetrate. This results in the desired closeness of the material fit connection, in such a way that the coating 26 adheres particularly firmly to the surface carrying it. In this context, the aforementioned porosity or roughening of the surface can be produced by a particularly suitable method, for example by etching—which may optionally be material-specific—by selectively setting a reinforcement zone of a material parameter or a crystallographic parameter or the like.

The enlarged detail in FIG. 11 shows schematically the material fit connection which can thereby be obtained of the coating 26 to the component which carries it, in the drawing the connection pin 10. The roughening of the surface of the connection pin, optionally in connection with a reinforcement region close to the surface, which can be produced for example by selective dissolution or etching away of individual material components, results in a connection zone 40, in which material from the coating 26 penetrates into the pores, surface holes or the like in the correspondingly prepared surface of the connection pin 10. Thus, in this connection zone 40, the materials of the connection pin 10, on the one hand, and the coating 26, on the other hand, are present together in such a way that they form a close meshing. A design of this type for applying a coating to a preferably ceramic material surface is further considered an inventive design in its own right, even for fields of application unrelated to dental implants.

LIST OF REFERENCE NUMERALS

1, 1', 1" dental implant system
2, 2', 2" first implant part
4 second implant part
6 outer thread
8 apical end
10 connection pin
12 receiving duct
14 indexing element
16 duct end piece
18 connecting screw
20 screw thread
22 spacer
24 surface 26 coating
28 inner surface
30a, b sub-coating
32a, b intermediate space
34 receiving chamber
36 groove
38 material chamber
40 connection zone

The invention claimed is:

1. A dental implant system, comprising:
a first implant part, provided for introduction into a jawbone,
a second implant part associated therewith, provided for attaching a tooth replacement part,
a connection pin mechanically interconnecting the implant parts, the connection pin integrally formed on one of the implant parts and which is insertable into a receiving duct provided in the other implant part, wherein the connection pin is formed of a material having a (Vickers) hardness of at least 500, and wherein the connection pin has a cross-section which tapers towards a free end of the connection pin, and is conical in shape,
a coating on a surface of the connection pin, the coating in a contact region with the receiving duct, an outer surface of the coating is configured to contact a surface of the receiving duct, the coating formed of a material softer than the material of the connection pin and having a layer thickness of at most 0.3 mm, the connection pin having a porous surface in the contact region to form a material fit connection to an inner surface of the coating, and the surface of the connection pin, in the contact region of the material fit connection to the coating, having an RA value of at most 10% of the layer thickness.

2. The dental implant system according to claim 1, wherein the porous surface is produced by an etching process and comprises a nanostructure having a plurality of pores or depressions having an average extent of less than 500 nm.

3. The dental implant system according to claim 1, wherein the connection pin, in the contact region provided with the coating, comprises below the coating a connection zone, in which material from the coating penetrates into the porous surface of the connection pin, and the materials of the connection pin and the coating are present together inside the connection zone, in such a way that they form a close meshing.

4. The dental implant system according to claim 1, in which the porous surface of the connection pin has a porosity of at least 0.1.

5. The dental implant system according to claim 1, wherein the connection pin is formed of a material having a (Vickers) hardness of at least 1000.

6. The dental implant system according to claim 1, wherein the coating is formed from a material having a (Vickers) hardness of at most 25.

7. The dental implant system according to claim 1, the connection pin having a non-round cross-section, having multiple symmetry, which is adapted to an internal cross-section of the receiving duct.

8. The dental implant system according to claim 1, the coating having a number of sub-coatings which are connected to the connection pin in a material fit.

9. The dental implant system according to claim 1, wherein the coating has a layer thickness between 0.001 mm and 0.2 mm.

10. The dental implant system according to claim 1, wherein the coating is produced from a plastics material.

11. The dental implant system according to claim 10, wherein the plastics material forming the coating has a modulus of elasticity of at least 1000 MPa.

12. The dental implant system according to claim 10, wherein the plastics material forming the coating has a water absorption of at most 1%.

13. The dental implant system according to claim 10, wherein the plastics material forming the coating has a softening point of at least 140° C.

14. The dental implant system according to claim 1, the connection pin having a roughened surface in the contact region having the coating.

15. The dental implant system according to claim 14, wherein the surface of the connection pin has an RA value of at most 5% of the layer thickness in the contact region of the material fit connection to the coating.

16. The dental implant system according to claim 1, the connection pin made of a ceramic material.

17. The dental implant system according to claim 1, the connection pin formed from zirconium oxide stabilised with yttrium oxide and/or aluminium oxide, the surface of the connection pin comprising, in the contact region of the material fit connection to the coating, a reinforcement zone having a reduced yttrium oxide or aluminium oxide content by comparison with an internal volume of the connection pin.

18. A method for producing a dental implant, comprising:
providing a first implant part for introduction into a jawbone,
providing a second implant part associated therewith for attaching a tooth replacement part,
mechanically interconnecting the implant parts with a connection pin formed on one of the implant parts, wherein the connection pin is insertable into a receiving duct provided in the other implant part, and wherein the connection pin is formed of a material having a (Vickers) hardness of at least 500,
applying a coating on a surface the connection pin, an outer surface of the coating is configured to contact a surface of the receiving duct, the coating in a contact region with the receiving duct, the coating formed of a material softer than the material of the connection pin and having a layer thickness of at most 0.3 mm, the connection pin having a porous surface in the contact region to form a material fit connection to an inner surface of the coating, and the surface of the connection pin, in the contact region of the material fit connection to the coating, having an RA value of at most 10% of the layer thickness,
roughening the surface of the connection pin in the contact region of the provided connection to the coating before the material fit connection to the coating is produced.

19. The method according to claim 18, wherein the roughening step is carried out by sandblasting.

20. The method according to claim 18, further comprising:
making the surface of the connection pin porous in the contact region of the provided connection to the coating before the material fit connection to the coating is produced.

21. The method according to claim 20, further comprising:
subjecting the connection pin to an etching process.

22. The method according to claim 18, further comprising:
applying and drying a dispersion to apply the coating to the connection pin.

23. The method according to claim 22, further comprising:
heat-treating, after the drying step, the connection pin at a treatment temperature of at least 350° C.

24. The dental implant system according to claim 6, wherein the coating is formed from a material having a (Vickers) hardness of at most 15.

25. The dental implant system according to claim 9, wherein the coating has a layer thickness between 0.05 mm and 0.1 mm.

26. The dental implant system according to claim 12, wherein the plastics material forming the coating has a water absorption of at most 0.2%.

27. The dental implant system according to claim 13, wherein the plastics material forming the coating has a softening point of at least 300° C.

28. The dental implant system according to claim 1, wherein said coating comprises a plurality of subcoatings and a plurality of intermediate spaces, wherein intermediate spaces of the plurality of intermediate spaces are positioned between subcoatings of the plurality of subcoatings.

29. The dental implant system according to claim 28, further comprising:
an adhesive that binds the connection pin in the receiving duct, wherein said adhesive is at least partially disposed in the plurality of intermediate spaces.

30. The dental implant system according to claim 1, wherein the receiving duct comprises a plurality of grooves, and grooves in the plurality of grooves are circumferentially oriented in the receiving duct, wherein the grooves are configured to receive an adhesive that binds the connection pin in the receiving duct.

31. A dental implant system, comprising:
a first implant part, provided for introduction into a jawbone,
a second implant part associated therewith, provided for attaching a tooth replacement part,
a connection pin mechanically interconnecting the implant parts, the connection pin integrally formed on one of the implant parts and which is insertable into a receiving duct provided in the other implant part, wherein the receiving duct is formed of a material having a (Vickers) hardness of at least 500, and wherein the connection pin has a cross-section which tapers towards a free end of the connection pin, and is conical in shape,
a coating on a surface of the receiving duct, the coating in a contact region with the connection pin, an outer surface of the coating is configured to contact a surface of the connection pin, the coating formed of a material softer than the material of the receiving duct and having a layer thickness of at most 0.3 mm, the receiving duct having a porous surface in the contact region to form a material fit connection to an inner surface of the coating, and the surface of the receiving duct, in the contact region of the material fit connection to the coating, having an RA value of at most 10% of the layer thickness.

* * * * *